United States Patent [19]

Hasegawa et al.

[11] Patent Number: 5,467,637

[45] Date of Patent: Nov. 21, 1995

[54] METHOD OF MEASURING GAS PURITY INFORMATION, CHAMBER UNIT AND EXPOSURE UNIT USING THE METHOD AND A DEVICE PRODUCTION METHOD

[75] Inventors: Takayuki Hasegawa, Yokohama; Hidehiko Fujioka, Yamato, both of Japan

[73] Assignee: Canon Kabushiki Kaisha, Tokyo, Japan

[21] Appl. No.: 168,150

[22] Filed: Dec. 17, 1993

[30] Foreign Application Priority Data

Dec. 24, 1992 [JP] Japan .................................. 4-344576
Jun. 24, 1993 [JP] Japan .................................. 5-153623

[51] Int. Cl.$^6$ .............................. G01N 29/02; G01N 7/00
[52] U.S. Cl. ........................ 73/24.01; 73/31.03; 73/23.2
[58] Field of Search ............................ 73/24.01, 24.05, 73/24.06, 31.03, 23.2

[56] References Cited

U.S. PATENT DOCUMENTS

| | | | |
|---|---|---|---|
| 3,194,054 | 7/1965 | Deaton et al. | 73/31.03 |
| 4,555,932 | 12/1985 | Crosby, Jr. | 73/24.01 |
| 4,662,212 | 5/1987 | Noguchi et al. | 73/24.01 |
| 5,060,506 | 10/1991 | Douglas | 73/24.01 |
| 5,060,507 | 10/1991 | Urmson et al. | 73/24.01 |
| 5,060,514 | 10/1991 | Aylsworth | 73/24.01 |
| 5,138,869 | 8/1992 | Tom | 73/31.03 |
| 5,214,952 | 6/1993 | Leggett et al. | 73/1 G |
| 5,313,820 | 5/1994 | Aylsworth | 73/24.01 |
| 5,325,703 | 7/1994 | Magori | 73/23.32 |

FOREIGN PATENT DOCUMENTS 2210977  6/1989  United Kingdom ................ 73/24.01

*Primary Examiner*—Hezron E. Williams
*Assistant Examiner*—J. David Wiggins
*Attorney, Agent, or Firm*—Fitzpatrick, Cella, Harper & Scinto

[57] ABSTRACT

The sonic velocity in a chamber which is filled with helium is measured by using ultrasonic waves, and the temperature in the chamber is also measured. Purity information relating to helium gas contained in the chamber is determined on the basis of the measured values of the sonic velocity and the temperature.

26 Claims, 6 Drawing Sheets

FIG. 1
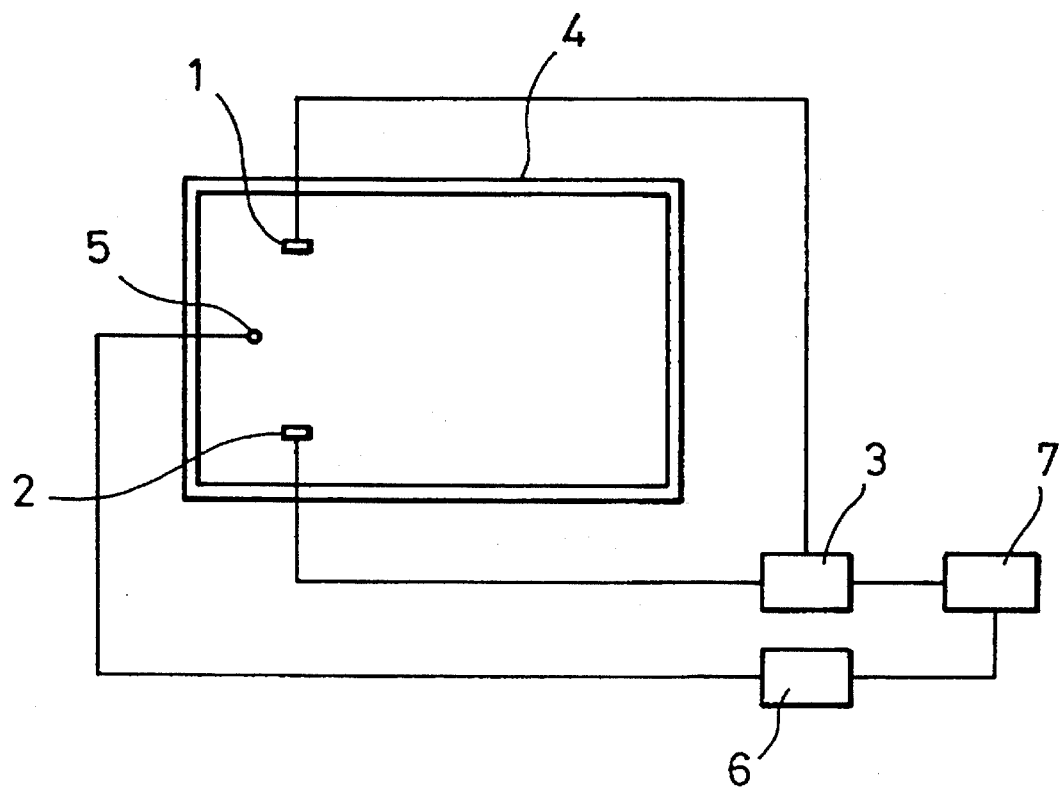
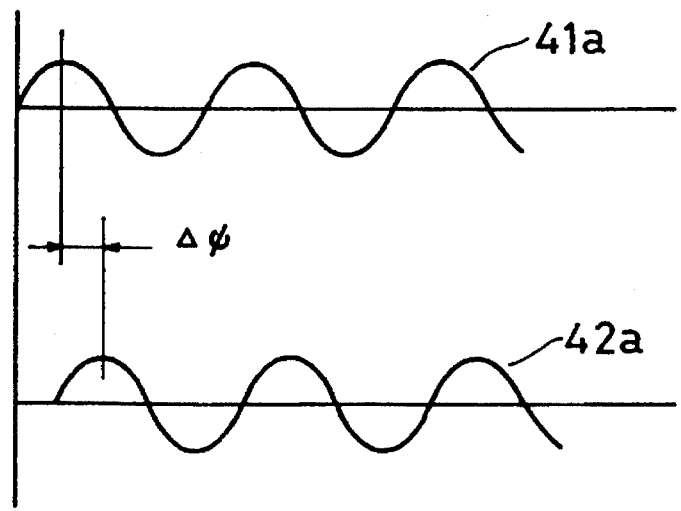
FIG. 2(a)
FIG. 2(b)

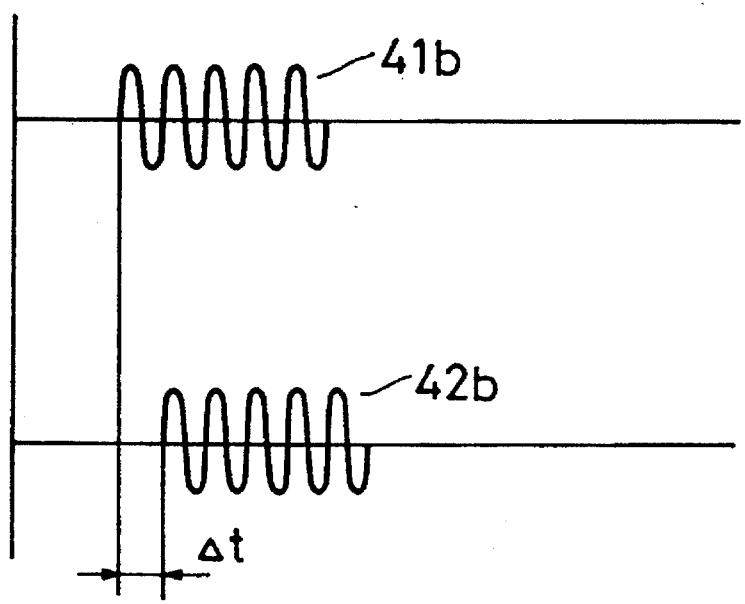
FIG. 3(a)
FIG. 3(b)
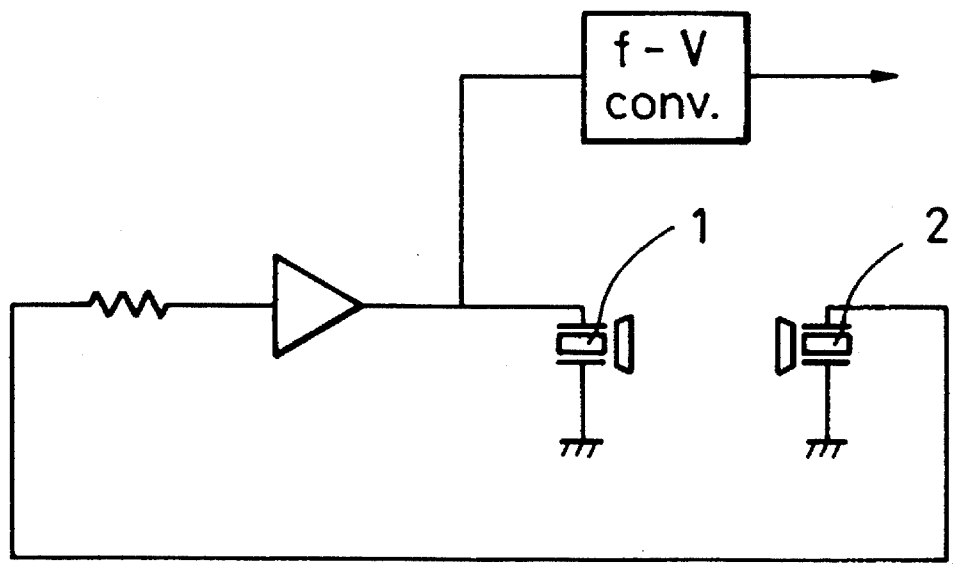
FIG. 4

METHOD OF MEASURING GAS PURITY INFORMATION, CHAMBER UNIT AND EXPOSURE UNIT USING THE METHOD AND A DEVICE PRODUCTION METHOD

BACKGROUND OF THE INVENTION

1. Field of the Invention

The present invention relates to a technique of determining information relating to purity of gas contained in a closed space.

2. Description of the Related Art

Conventional methods of measuring information relating to purity of gas in a closed space include the following:

(1) a method of directly measuring the purity of gas such as oxygen ($O_2$) or the like, which can be easily and directly measured with respect to its concentration by a sensor; and (2) a method of predicting the purity of gas in a container from the results of measuring the concentration of a specified gas component in gases that leak into a closed space when a large measurement apparatus (for example, a gas flow meter, a mass spectrometer or the like) is required for measuring the concentration of an inert gas such as helium (He) or the like.

However, the conventional methods have the problem that the purity of an inert gas such as helium cannot be easily or precisely measured.

SUMMARY OF THE INVENTION

The present invention has been achieved to solve the above-noted problem. It is an object of the present invention to provide a method which can precisely and easily measure gas purity information even if the presence of gas cannot be measured directly, such as in the case of helium gas.

It is another object of the present invention to provide an exposure unit which employs such a measurement method, and to provide a semiconductor device production method.

In order to achieve these objects, a method of the present invention for measuring purity information relating to gas contained in a closed space comprises generating ultrasonic waves in the gas contained in the closed space; measuring the sonic velocity in the gas contained in the closed space, and determining purity information relating to the gas in the closed space on the basis of the measured value.

A chamber unit of the present invention for measuring purity information relating to gas contained in a closed space comprises a chamber having a closed space for containing gas, means for generating ultrasonic waves in the chamber contained in the closed space, sonic velocity measurement means for measuring the sonic velocity in the gas contained in the chamber and determination means for determining purity information relating to the gas in the chamber, on the basis of the value measured by the sonic velocity measurement means.

An exposure unit of the present invention comprises a chamber containing a substrate in a gaseous ambience, means for exposing the substrate, means for generating ultrasonic waves in the gas contained in the chamber, sonic velocity measurement means for measuring the sonic velocity in the gas in the chamber, and determination means for determining purity information relating to the gas in the chamber, on the basis of the value measured by the sonic velocity measurement means.

A device production method of the present invention comprises the steps of containing a substrate in a gaseous ambience in a chamber, generating ultrasonic waves in the gas contained in the chamber, measuring the sonic velocity in the gas in the chamber, determining purity information relating to the gas in the chamber, on the basis of the measured value of the sonic velocity, and transferring a circuit pattern onto the substrate by exposure to an enteractive energy field or source.

BRIEF DESCRIPTION OF THE DRAWINGS

FIG. 1 is a drawing illustrating the configuration of an embodiment of the present invention;

FIGS. 2(a) and 2(b) are drawings illustrating a first method of measuring the sonic velocity of a particular gas;

FIGS. 3(a) and 3(b) are drawings illustrating a second method of measuring the sonic velocity of a particular gas;

FIG. 4 is a drawing illustrating a third method of measuring the sonic velocity of a particular gas;

Like reference numerals indicate like elements throughout the figures.

DESCRIPTION OF THE PREFERRED EMBODIMENTS

Figure 5:
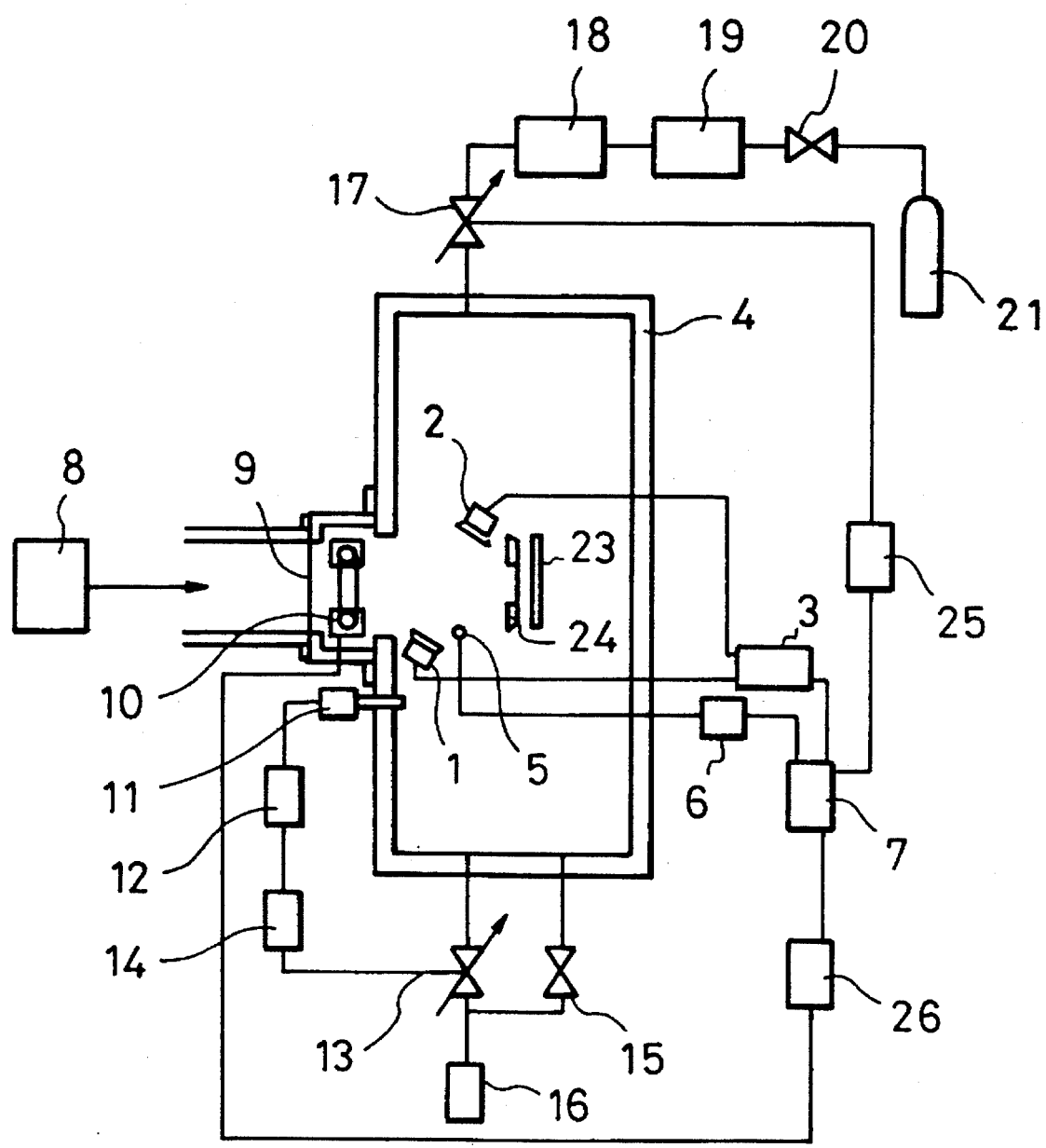
FIG. 5 is a drawing illustrating the configuration of an exposure device in accordance with a second embodiment of the present invention.

A first embodiment of the present invention will now be described.

FIG. 1 is a drawing showing the configuration of an apparatus for measuring gas purity information in accordance with a first embodiment of the present invention.

In FIG. 1, reference numeral 1 denotes an oscillation element for generating ultrasonic waves; and reference numeral 2 denotes a detection element for receiving the ultrasonic waves. Reference numeral 3 denotes a sonic velocity measurement circuit connected to the oscillation element 1 and the detection element 2 so as to measure the sonic velocity $a_1$. Reference numeral 4 denotes a chamber which forms a closed space; reference numeral 5, a temperature measurement element; reference numeral 6, a temperature measurement circuit; and reference numeral 7, a purity computing circuit for calculating the purity of gas contained in chamber 4 from the measured sonic velocity and temperature.

The method of measuring the sonic velocity $a1$ is described below. The sonic velocity measurement circuit 3 receives the ultrasonic wave generated from the oscillation element 1 through the detection element 2, and measures a delay from the generated sonic wave to determine the sonic velocity $a_1$. There are several possible methods of measuring velocity of a sonic wave FIGS. 2(a), 2(b), 3(a), 3(b) and 4 respectively show examples of these methods.

In the example shown in FIGS. 2(a) and 2(b), a phase difference $\Delta\psi$ between the ultrasonic wave 41a generated from the oscillation element 1 and the ultrasonic wave 42a received by the detection element 2 is measured, and the sonic velocity $a_1$ is determined from a distance L between the oscillation element 1 and the detection element 2. In this case, the frequency of the ultrasonic wave generated is preferably about 40 kHz.

In the example shown in FIGS. 3(a) and 3(b), the oscillation element 1 generates a burst wave 41b, and the sonic velocity $a_1$ is determined from a delay time $\Delta t$ of the sonic wave 42b detected by the detection element 2 and the distance L between the oscillation element 1 and the detection element 2.

In the example shown in FIG. 4, the sonic velocity $a_1$ is determined from a variation $\delta n$ in resonance frequency by using the Oscillation element 1 an the detection element 2 in a phase delay circuit portion of an oscillation circuit.

When the sonic velocity $a_1$ is determined by any one of the above methods, the temperature in the chamber 4 is previously measured by the temperature measurement element 5 and determined by the temperature measurement circuit 6.

The theoretical sonic velocity $a_2$ in a particular gas is theoretically determined by the type of the relevant gas and the temperature, as shown by the following equation:

$$a_2 = \sqrt{\gamma RT}$$

($\gamma$: ratio of specific heats at constant pressure and constant volume of gas, R: gas constant, T: absolute temperature).

If different gases are mixed in a ratio of x:y, the ratio of specific heat $\gamma$ and the gas constant R are approximated by using the following equations:

$$\gamma = \frac{x}{x+y}\gamma x + \frac{y}{x+y}\gamma y$$

($\gamma x$: ratio of specific heat of gas x, $\gamma y$: ratio of specific heat of gas y)

$$R = \frac{x}{x+y}R_x + \frac{y}{x+y}R_y$$

($R_x$: ratio of specific heat of gas x, $R_y$: ratio of specific heat of gas y)

For example, when the chamber 4 is filled with helium gas, air is mixed in the chamber 4, and the temperature is 29.15 K. (23° C.), the theoretical sonic velocity $a_2'$ in helium gas with a purity of 99.99% is 1013 m/s, and the theoretical sonic velocity $a_2''$ in helium gas with a purity of 99.00% is 1008 m/s.

The method of determining the purity of the gas in the closed space by using the sonic velocity $a_1$ determined by the above method is described below.

When the gas mixed in the chamber 4 can be specified, the purity of the gas in the chamber 4 can be determined from the measured sonic velocity $a_1$ by computation. This computation is performed by the purity computing circuit 7. The as purity x (%) is determined from the measured sonic velocity $a_1$ (m/s) and the temperature T (K.) by the following equation:

$$x = 100 \times \left\{ \frac{-(\gamma_x R_y + \gamma_y R_x - 2\gamma_y R_y) \pm \sqrt{(\gamma_x R_y + \gamma_y R_x - 2\gamma_y R_y)^2 - 4(\gamma_x - \gamma_y)(R_x - R_y)\left(\gamma_y R_y - \frac{a_1^2}{T}\right)}}{2(\gamma_x - \gamma_y)(R_x - R_y)} \right\}$$

For example, if the chamber 4 is filled with helium gas, air is mixed in the chamber 4, the measured sonic velocity $a_1$ is 1010 m/s, and the temperature T is 296.15 K. (23° C.), the following values are obtained:

helium (23° C.): $\gamma_x$=1.667 $R_x$=2078 (J/kg.K)

air (23° C.): $\gamma_y$=1.402 $R_y$=2887 (J/kg.K)

These values are substituted in the above equation to determine the purity x of helium in the chamber 4, as follows:

x=99.44

Even if the type of the gas mixed in the chamber 4 cannot be specified, a decision is made by comparison between the measured sonic velocity $a_1$ and the theoretical sonic velocity $a_2$ at the temperature of measurement whether or not both velocities agree to detect the presence of a purity variation.

This embodiment has the following effects:

(1) Purity information relating to a particular gas can be obtained regardless of the type of the gas.

(2) The whole apparatus can be made compact.

A second embodiment of the present invention will now be described.

An embodiment of an exposure unit for producing a device using the aforementioned method of measuring gas purity is described below.

In FIG. 5, members 1 to 7 have the same functions as those described above with reference to FIG. 1. Reference numeral 8 denotes a radiation source that emits X-ray light for exposure. An SOR Dynchration Orbital Radiation light source is preferably used as the radiation source 8. Reference numeral 9 denotes an X-ray passing window made of a metal (for example, beryllium) which absorbs little of the X-rays; reference numeral 10, an exposure shutter for controlling exposure; reference numeral 11, a pressure gauge; reference numeral 12, a controller for controlling the pressure gauge 11; reference numeral 13, a control valve having variable conductance; and reference numeral 14, a controller for controlling the control valve 13. Reference numeral 15 denotes a bypass valve; reference numeral 16, a vacuum suction pump; reference numeral 17, a variable flow regulating valve; reference numeral 18, a mass flow meter for measuring the amount of helium supplied; and reference numeral 19, a constant temperature bath. Reference numeral 20 denotes a helium main valve, and reference numeral 21 denotes a helium container for supplying high-purity helium gas. Reference numeral 23 denotes wafer as a semiconductor substrate, and reference numeral 24 denotes a mask having a transfer circuit pattern formed thereon, both of which are held and contained in the chamber 4 during exposure. Reference numeral 25 denotes a driver for driving the flow regulating valve 17, and reference numeral 26 denotes an operation control circuit provided with a computer for computing the amount of the X-rays absorbed by the helium, and for driving the exposure shutter 10.

In the unit of this embodiment, in an exposure operation, helium which fills the chamber 4 must be kept at high purity, a constant temperature, constant pressure and a reduced pressure atmosphere at a level high enough to inhibit X-ray attenuation and exposure variation as much as possible, while maintaining the precision of the whole apparatus. An operation for maintaining the helium in a constant state is described below.

The bypass valve 15 is first opened, and the pressure in the chamber 4 is reduced to a predetermined pressure (in this embodiment, $1 \times 10^{-3}$ Torr) by the vacuum suction pump 16. The bypass valve 15 is then closed, and the main valve 20 is opened. High-purity helium supplied from the helium container 21 and kept at a constant temperature by the constant temperature bath 19 is introduced into the chamber 4 to a predetermined pressure (in this embodiment, 150 Torr). The helium is then caused to flow at a flowrate regulated by the flow regulating valve 17, and the conductance of the control valve 13 is adjusted so that the pressure in the chamber 4 is kept constant on the basis of a signal from the pressure gauge 11.

The purity of the helium in the chamber 4 is determined in the purity computing circuit 7 by the method described above in the first embodiment. The flowrate of the high-purity helium is changed by regulating the opening of the flow regulating valve 17 through the driver 25 on the base of the signal from the purity computing circuit 7. Feedback control is then made so that the helium purity in the chamber 4 is maintained within a predetermined range. At this time, in order to inhibit pressure variation in the chamber 4 caused by a variation in the helium flow, the pressure in the chamber 4 can be maintained within a predetermined range by feedback control of the conductance of the control valve 13 on the basis of the signal from the pressure gauge 11.

In this way, the exposure operation is started in a state in which the chamber pressure 4 is maintained constant. In the exposure operation, the exposure shutter 10 is opened, and the circuit pattern on the mask 24 is transferred to the wafer 23 by exposure by applying X-rays to the mask 24. The amount of the X-rays absorbed by the helium is calculated by the operation control circuit 26, and the opening time of the exposure shutter 22 is controlled so that the exposure of the wafer surface is constant regardless of the purity according to the results of the computation.

This embodiment has the following effects:

(1) The helium purity can be controlled with high precision, and high-precision-exposure can thus be performed.

(2) The exposure can be controlled with high precision by measuring the helium purity and controlling the opening time of the exposure time during exposure.

A third embodiment of the present invention will now be described.

Figure 6:
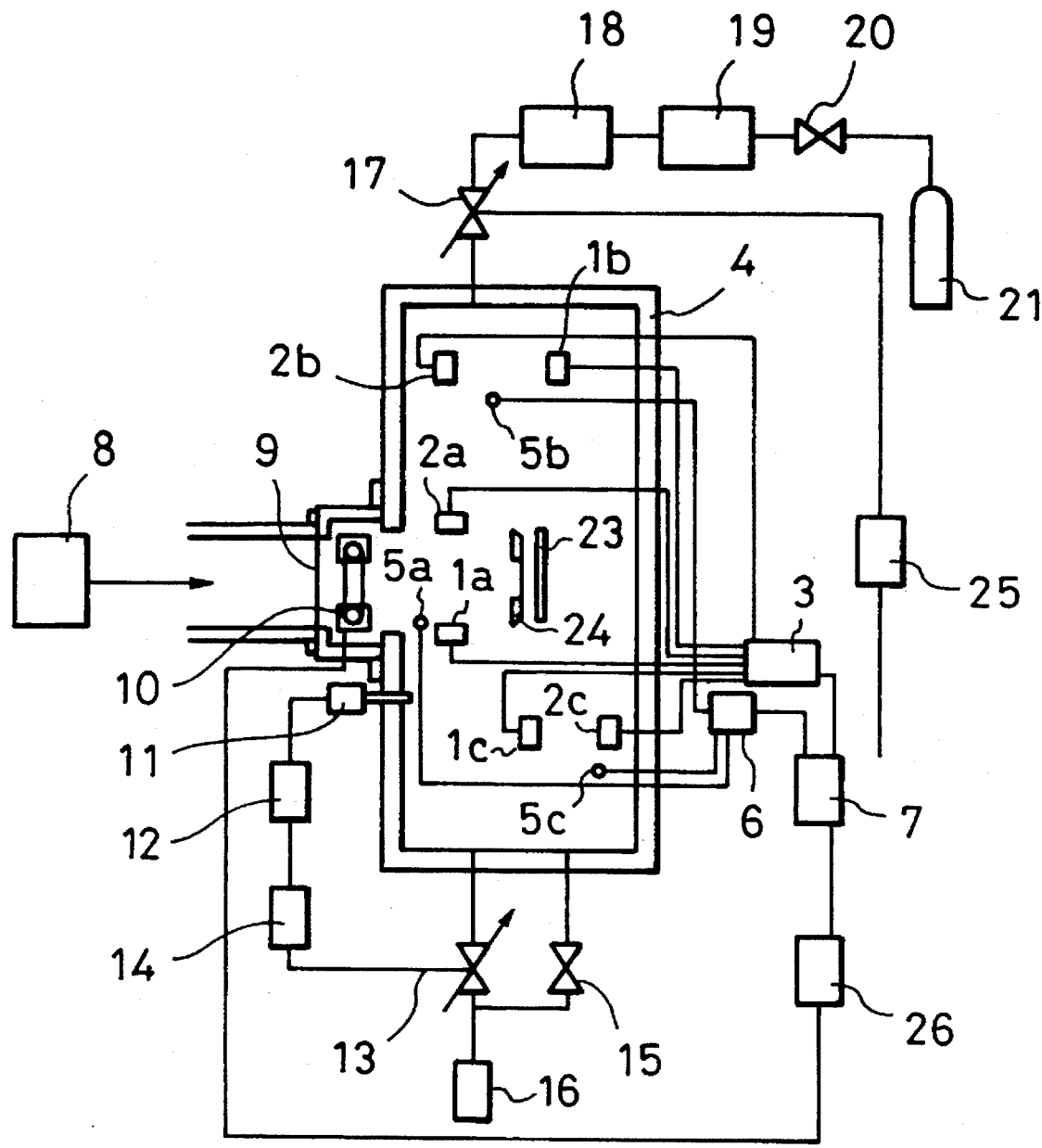
FIG. 6 is a drawing illustrating the configuration of an exposure device in accordance with a third embodiment of the present invention.

FIG. 6 shows a modified embodiment of the embodiment shown in FIG. 5. The same reference numerals as those in FIG. 5 denote like members. This embodiment is characterized by measuring gas purity at three positions in the chamber 4. This embodiment thus comprises an ultrasonic oscillation element 1a, an ultrasonic detection element 2a and a temperature measurement element 5a, which are disposed near the exposure beam path in the vicinity of the center of the chamber 4; an ultrasonic oscillation element 1b, an ultrasonic detection element 2b and a temperature measurement element 5b, which are disposed near the upper portion in the chamber 4; and an ultrasonic oscillation element 1c, an ultrasonic detection element 2c and a temperature measurement element 5c, which are disposed near the lower portion in the chamber 4. Each of the ultrasonic oscillation elements and the ultrasonic detection elements is connected to the sonic velocity measurement circuit 3, and each of the temperature measurement elements is connected to the temperature measurement circuit 6.

The purity computing circuit 7 computes the purity information relating to the helium gas at the three positions in the chamber, i.e., computes the gas purity distribution in the chamber 4, by the method described above. The gas purity in the chamber is controlled by using the gas purity information at a predetermined position, or an average of the gas purity information at the three positions, and the mask pattern is transferred to the wafer by exposure.

This embodiment permits more precise control of the gas purity, and thus high-precision exposure.

A fourth embodiment of the present invention will now be described.

Figure 7:
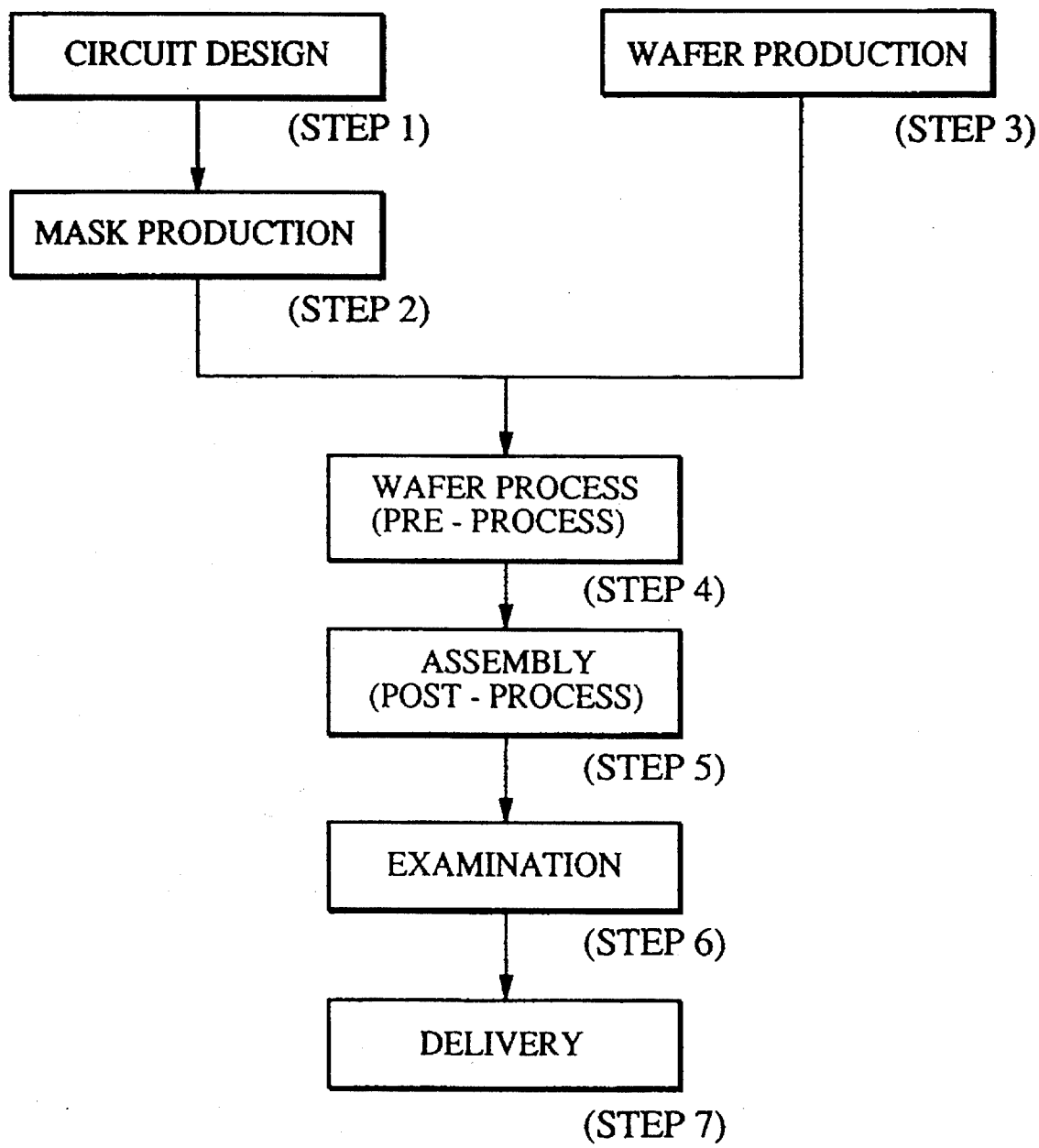
FIG. 7 is a flowchart illustrating a process for producing a semiconductor device.

An embodiment of a device production method which employs the above-described exposure unit is described below. FIG. 7 is a flowchart showing production of a semiconductor device (for example, a semiconductor chip such as an IC or LSI, a liquid crystal panel or CCD). The circuit of a semiconductor device is designed in Step 1 (circuit design), and a mask on which the designed circuit pattern is formed is produced in Step 2 (mask production). On the other hand, a wafer is produced by using a material such as silicon or the like in Step 3 (wafer production). In Step 4 (wafer process), which is referred to as a "pre-process", an actual circuit is formed on the wafer by lithography using the prepared mask and wafer. In Step 5 (assembly), which is referred to as a "post-process", a semiconductor chip is formed by using the wafer produced in Step 4. This process include the assembly process (dicing and bonding), a packaging process (chip sealing) and so on. In step 6 (examination), the semiconductor device produced in Step 5 is examined by an operation verification test, or a durability test, for example. The semiconductor device is completed through these steps and is delivered (Step 7).

Figure 8:
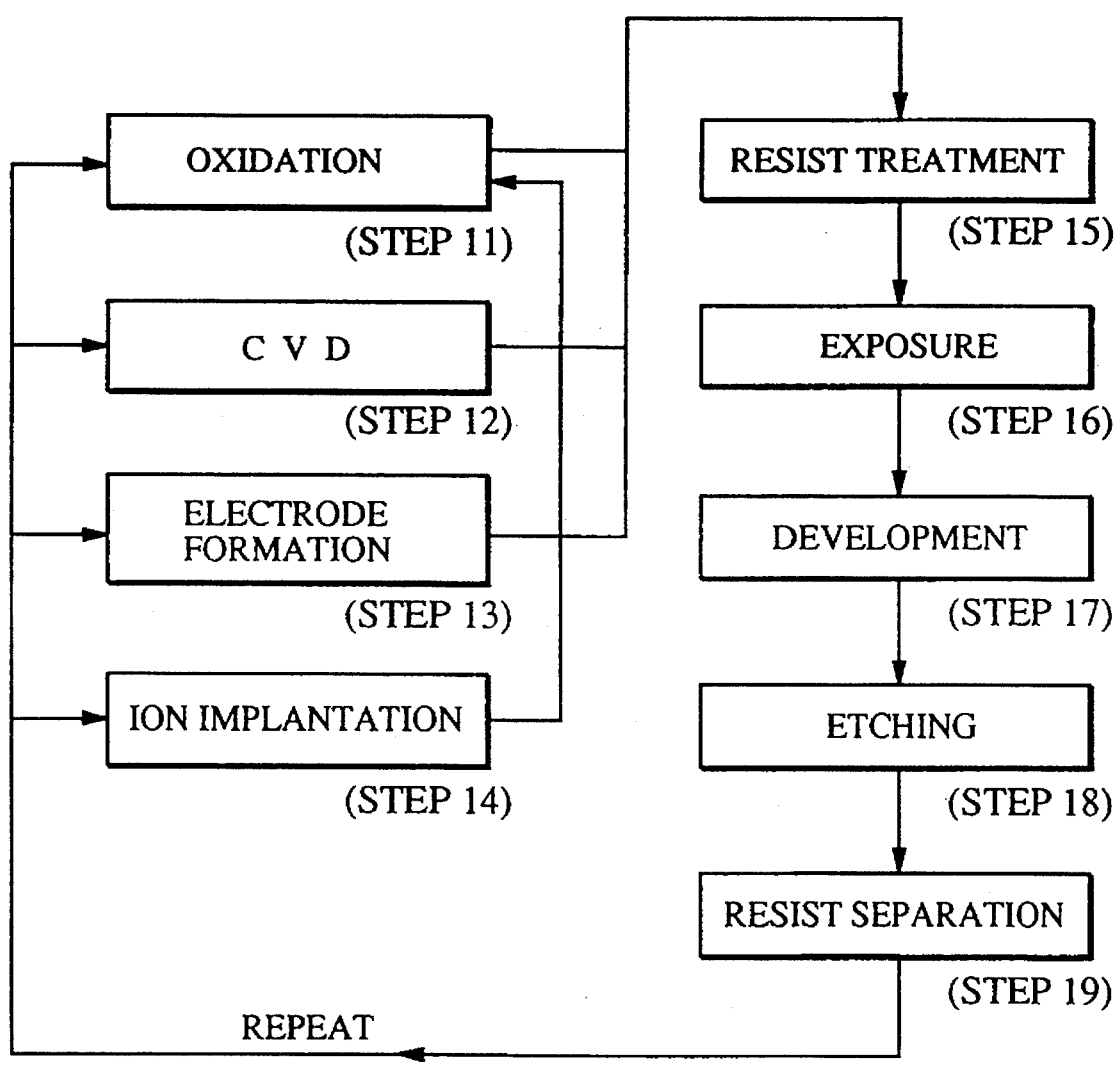
FIG. 8 is a flowchart illustrating a wafer process of the present invention in detail.

FIG. 8 is a flowchart showing details of the wafer process (Step 4 shown in FIG. 7). The surface of the wafer is oxidized in Step 11 (oxidation). An insulating film is formed on the wafer surface in Step 12 by a chemical vapor deposition method (CVD). An electrode is formed by evaporation in Step 13 (electrode formation). Ions are implanted in the wafer in Step 14 (ion implantation). A sensitizing agent is coated on the wafer in Step 15 (resist treatment). The circuit pattern of the mask is printed by exposure on the wafer using the above-described exposure unit in Step 16 (exposure). The exposed wafer is developed in Step 17 (development). Portions other than the developed resist image are cut off in Step 18 (etching). After etching, the unnecessary resist is removed in Step 19 (resist separation). These steps are repeated to form multiple circuit patterns on the wafer.

The production method of this embodiment can produce a highly integrated semiconductor device which cannot easily be produced by a conventional method.

Except as otherwise disclosed herein, the various components shown in outline or in block form in the figures are individually well known in this art and their internal construction and operation are not critical either to the making or using of this invention or to a description of the best mode of the invention.

While the present invention has been described with respect to what is at present considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of measuring purity information relating to gas contained in a closed space, said method comprising:

generating ultrasonic waves in the gas contained in the closed space;

measuring values of the sonic velocity in the gas at a plurality of positions in the closed space; and determining purity information relating to the gas in the closed space on the basis of the measured values.

2. A method according to claim 1, further comprising measuring the temperature of the gas contained in the closed space during said measuring step, and determining the gas purity information on the basis of the measured temperature and sonic velocity.

3. A chamber unit for measuring purity information relating to gas contained in a closed space, comprising:

an airtight chamber having a closed space for containing gas;

means for generating ultrasonic waves in the gas contained in said closed space;

sonic velocity measurement means for measuring values of the sonic velocity in the gas at a plurality of positions in said chamber; and determination means for determining purity information relating to the gas in said chamber, on the basis of the values measured by said sonic velocity measurement means.

4. A chamber unit according to claim 3, further comprising temperature measurement means for measuring the temperature in said closed space.

5. A chamber unit according to claim 4, wherein said determination means determines the gas purity information on the basis of the measured sonic velocity and temperature.

6. An exposure unit comprising:

an airtight chamber containing a substrate in a gaseous ambience;

exposing means for exposing said substrate to an interactive energy field or source;

means for generating ultrasonic waves in the gas contained in said chamber;

sonic velocity measurement means for measuring values of the sonic velocity in the gas at a plurality of positions in said chamber; and determination means for determining purity information relating to the gas in said chamber, on the basis of the values measured by said sonic velocity measurement means.

7. An exposure unit according to claim 6, further comprising gas purity control means for maintaining the gas purity in said chamber constant, according to the determined gas purity information.

8. An exposure unit according to claim 6, further comprising exposure control means for controlling exposure according to the determined gas purity information.

9. An exposure unit according to claim 6, wherein said sonic velocity measurement means is provided near an exposure beam that exposes the substrate.

10. A device production method comprising the steps of:

containing a substrate in a gaseous ambience in a chamber;

generating ultrasonic waves in the gas contained in the chamber;

measuring values of the sonic velocity in the gas at a plurality of positions in the chamber;

determining purity information relating to the gas in the chamber, on the basis of the measure values of the sonic velocity; and transferring a circuit pattern from a reference mask onto the substrate by exposure to an interactive energy field or source when the chamber is assessed to contain gas of sufficiently high purity for high quality device production.

11. A method according to claim 10, further comprising controlling exposure in said transferring step on the basis of the determined gas purity information.

12. An apparatus according to claim 6, wherein said exposing means exposes the substrate with X-rays.

13. A method according to claim 10, wherein said transferring step comprises transferring the circuit pattern from a reference mask by X-ray exposure.

14. A method of measuring purity information relating to reduced pressure gas contained at least at moderate vacuum levels in a closed space, said method comprising:

generating ultrasonic waves in the reduced pressure gas contained in the closed space;

measuring the value of sonic velocity in the reduced pressure gas in the closed space; and determining purity information relating to the reduced pressure gas in the closed space on the basis of the measured value.

15. A method according to claim 14, further comprising measuring the temperature of the reduced pressure gas contained in the closed space during said measuring step, and determining the gas purity information on the basis of the measured temperature and sonic velocity.

16. A chamber unit comprising:

a vacuum chamber having a closed space for containing reduced pressure gas at least moderate vacuum levels;

means for generating ultrasonic waves in the reduced pressure gas contained in said closed space;

sonic velocity measuring means for measuring the value of sonic velocity in the reduced pressure gas in said chamber; and determination means for determining purity information relating to the reduced pressure gas in said chamber, on the basis of the value measured by said sonic velocity measurement means.

17. A chamber unit according to claim 16, further comprising temperature measurement means for measuring the temperature of the reduced pressure gas in said closed space.

18. A chamber unit according to claim 17, wherein said determination means determines the gas purity information on the basis of the measured sonic velocity and temperature.

19. An exposure apparatus comprising:

a vacuum chamber containing a substrate in a reduced pressure gaseous ambience at least at moderate vacuum levels;

exposing means for exposing the substrate to an interactive energy field or source;

means for generating ultrasonic waves in the reduced pressure gas contained in said chamber;

sonic velocity measuring means for measuring the value of sonic velocity in the reduced pressure gas in said chamber; and determination means for determining purity information relating to the reduced pressure gas in said chamber, on the basis of the value measured by said sonic velocity measurement means.

20. An exposure apparatus according to claim 19, further comprising gas purity control means for maintaining the gas purity of the reduced pressure gas in said chamber constant, according to the determined gas purity information.

21. An exposure apparatus according to claim 19, further comprising exposure level control means for controlling the degree of exposure according to the determined gas purity information.

22. An exposure apparatus according to claim 19, wherein said sonic velocity measurement means is provided near an exposure beam that exposes the substrate to an interactive energy field.

23. An apparatus according to claim 19, wherein said exposing means exposes the substrate with X-rays.

24. A device production method comprising the steps of:

containing a substrate in a reduced pressure gaseous ambience at least moderate vacuum levels in an airtight chamber;

generating ultrasonic waves in the reduced pressure gas contained in the chamber;

measuring the value sonic velocity in the reduced pressure gas in the chamber;

determining purity information relating to the reduced pressure gas in the chamber, on the basis of the measured value of the sonic velocity; and transferring a circuit pattern from a reference mask onto the substrate by exposure.

25. A device production method according to claim 24, further comprising controlling the level of exposure in said transferring step on the basis of the determined gas purity information.

26. A method according to claim 24, wherein said transferring step comprises transferring the circuit pattern from a reference mask by X-ray exposure.

* * * * *

UNITED STATES PATENT AND TRADEMARK OFFICE
CERTIFICATE OF CORRECTION

PATENT NO. : 5,467,637
DATED : November 21, 1995
INVENTOR(S) : Hasegawa et al.

It is certified that error appears in the above-indentified patent and that said Letters Patent is hereby corrected as shown below:

COLUMN 2:

Line 8, "pattern" should read --pattern from a reference mask--.
Line 56, "al" should read --$a_1$--.

COLUMN 3:

Line 8, "$\Delta$ t" should read --$\Delta t$--.
Line 22, "variation6n" should read --variation--.

COLUMN 4:

Line 27, "x = 99.44" should read --x = 99.44%--.
Line 46, "SOR Dynchration Orbital Radiation" should read --SOR (Synchrotron Orbital Radiation)--.

COLUMN 8:

Line 21, "An apparatus" should read --An exposure unit--.

Signed and Sealed this

Seventh Day of May, 1996

Attest:

BRUCE LEHMAN

Attesting Officer    Commissioner of Patents and Trademarks